United States Patent
Emoto

(10) Patent No.: US 10,435,335 B2
(45) Date of Patent: Oct. 8, 2019

(54) METHOD FOR PRODUCING ALPHA-OLEFIN LOW POLYMER

(71) Applicant: Mitsubishi Chemical Corporation, Chiyoda-ku (JP)

(72) Inventor: Hiroki Emoto

( * ) Notice: Subject to any disclaimer, the term of this patent is extended or adjusted under 35 U.S.C. 154(b) by 0 days.

(21) Appl. No.: 15/714,415

(22) Filed: Sep. 25, 2017

(65) Prior Publication Data

US 2018/0009728 A1    Jan. 11, 2018

Related U.S. Application Data

(63) Continuation of application No. PCT/JP2016/057860, filed on Mar. 11, 2016.

(30) Foreign Application Priority Data

Mar. 25, 2015    (JP) .................................. 2015-062877

(51) Int. Cl.
  *C07C 2/32*    (2006.01)
  *C07C 7/04*    (2006.01)
  (Continued)

(52) U.S. Cl.
  CPC .................. *C07C 2/32* (2013.01); *C07C 7/04* (2013.01); *C08F 6/12* (2013.01); *C07C 2531/02* (2013.01);
  (Continued)

(58) Field of Classification Search
  None
  See application file for complete search history.

(56) References Cited

U.S. PATENT DOCUMENTS

| 6,891,061 B1 * | 5/2005 | Nishimura | ............ B01D 3/324 |
| | | | 560/218 |
| 2003/0073595 A1 * | 4/2003 | Dorton | ................. C11D 7/5027 |
| | | | 510/188 |

(Continued)

FOREIGN PATENT DOCUMENTS

| JP | 7-149671 | 6/1995 |
| JP | 2003-261602 | 9/2003 |
| JP | 2012-188371 | 10/2012 |
| JP | 2013-170135 | 9/2013 |
| JP | 2014-159391 | 9/2014 |

(Continued)

OTHER PUBLICATIONS

International Search Report dated Jun. 7, 2016 in PCT/JP2016/057860, filed on Mar. 11, 2016 ( with English Translation).

(Continued)

*Primary Examiner* — In Suk C Bullock
*Assistant Examiner* — Ali Z Fadhel
(74) *Attorney, Agent, or Firm* — Oblon, McClelland, Maier & Neustadt, L.L.P.

(57) ABSTRACT

An object of the present invention is to provide a method for suppressing the precipitation of polymers with a high concentration dissolved in a solvent in the operation termination step and suppressing the blockage of the apparatus by the polymers even when the polymers with a high concentration are precipitated, and the invention relates to a method for producing an α-olefin low polymer comprising a production operation step and an operation termination step, wherein the supply position of a supply liquid to a distillation column in the operation termination step is changed to a position lower than the supply position of a supply liquid to the distillation column in the production operation step.

20 Claims, 1 Drawing Sheet

(51) Int. Cl.
 *C08F 6/12* (2006.01)
 *C08L 23/08* (2006.01)
 *C07C 11/107* (2006.01)

(52) U.S. Cl.
 CPC ...... *C07C 2531/14* (2013.01); *C07C 2531/18* (2013.01); *C07C 2531/22* (2013.01)

(56) References Cited

U.S. PATENT DOCUMENTS

| | | | |
|---|---|---|---|
| 2006/0135832 A1* | 6/2006 | Vora | B01D 3/14 585/517 |
| 2010/0030000 A1* | 2/2010 | Emoto | C08F 10/00 585/512 |
| 2013/0178645 A1 | 7/2013 | Shinohata et al. | |
| 2016/0206970 A1* | 7/2016 | Alzner | B01D 3/008 |

FOREIGN PATENT DOCUMENTS

| | | |
|---|---|---|
| JP | 2015-74617 | 4/2015 |
| TW | 201414530 A | 4/2014 |
| WO | WO 2012/115110 A1 | 8/2012 |

OTHER PUBLICATIONS

Written Opinion dated Jun. 7, 2016 in PCT/JP2016/057860, filed on Mar. 11, 2016.
Russian Office Action dated Jan. 15, 2019, in Russian Patent Application No. 2017132830/04 (057724) (with English Translation).
Examination Report (Office Action) dated Nov. 19, 2018, in GCC Patent Application No. GCC 2016-31051.
Taiwanese Office Action dated Jun. 28, 2019, in Taiwanese Patent Application No. 105109405 (with English Translation).

* cited by examiner

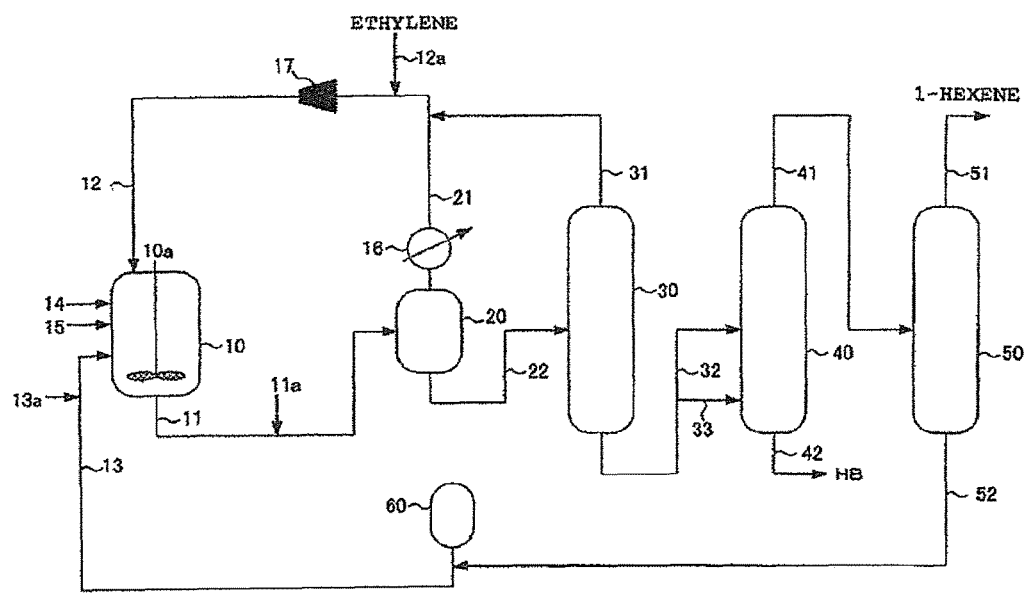

METHOD FOR PRODUCING ALPHA-OLEFIN LOW POLYMER

TECHNICAL FIELD

The present invention relates to a method for producing an α-olefin low polymer. An α-olefin low polymer is a useful substance which is widely used as a raw material for a monomer of olefin polymers, as a comonomer of various polymers, and as a raw material for plasticizers, surfactants, lubricants, and the like. Particularly, 1-hexene obtained by a low polymerization reaction of ethylene is useful as a raw material for linear low density polyethylene.

BACKGROUND ART

An α-olefin low polymer is produced by a method of subjecting a raw material α-olefin to a low polymerization reaction in the presence of a catalyst such as a homogeneous catalyst and a solvent, but on this occasion, by-product polymers such as polyethylene adhere to the reaction system such as the reactor.

Patent Document 1 discloses a method of performing the reaction under such conditions that the shape of the polymers becomes granule shape, centrifuging the reaction liquid containing the granule-shaped polymers to separate the solid matter, and discharging the separated solid matter with a rotating screw out of the system.

Patent Document 2 discloses a method of performing operation so that the temperature of the reaction liquid in the process lines where the polymers are present is controlled to a temperature range where the adhesion and precipitation of the polymers do not occur.

Patent Document 3 discloses dissolution in a solvent under an atmosphere of a pressure lower than the partial pressure of the raw material α-olefin at the time of the low polymerization reaction, in order to efficiently remove the polymers adhered to the equipments for the low polymerization reaction of the α-olefin.

BACKGROUND ART DOCUMENT

Patent Document

[Patent Document 1] JP-A-7-149671
[Patent Document 2] JP-A-2003-261602
[Patent Document 3] JP-A-2013-170135

SUMMARY OF THE INVENTION

Problems that the Invention is to Solve

However, in the method described in Patent Document 1, there is not disclosed a separation method of the polymers dissolved in the solvent and the method requires an expensive solid-liquid separation apparatus, so that construction costs increase. In the method described in Patent Document 2, when it is intended to maintain the process at a temperature at which the polymers do not precipitate, it becomes a limitation for optimum design of e.g., a distillation column and the construction costs tend to increase. Also, the adhesion and precipitation of the polymers are unavoidable but any coping method at that time is not disclosed at all. Patent Document 3 does not disclose any efficient cleaning process capable of discharging the polymers from the process without blockage.

In an industrial production method of the α-olefin low polymer, there is a case where the polymers are formed as by-products, they do not dissolve in a solvent to precipitate, and further adhere to the reactor, a heat exchanger, and the like. It is also important not to form the polymers as by-products and not to precipitate the polymers, but there is a case where the polymers are unavoidably formed as by-products and precipitated. For example, in the operation termination step, the polymers may be unavoidably precipitated.

In the industrial production method of the α-olefin low polymer, even when the polymers are precipitated, it is desirable that they are discharged from the process without adhesion to the production apparatus or the polymers are discharged from the process without blocking the production apparatus even when the polymers are slightly adhered.

Accordingly, the present invention is made in consideration of the above circumstances. That is, an object of the invention is to provide a method for suppressing the precipitation of the polymers dissolved in a solvent in a high concentration in the operation termination step and is to provide a method for suppressing the blockage of the apparatus by the polymers in the α-olefin low polymer production apparatus even when the polymers dissolved in the solvent in a high concentration are precipitated caused by temperature drop or the like.

Moreover, another object of the invention is to provide a convenient and efficient separation method of the polymers.

Furthermore, still another object of the invention is to provide a convenient and efficient cleaning method of a reactor and/or a heat exchanger.

Means for Solving the Problems

As a result of extensive studies, the present inventors have found that the above problems can be solved by setting the supply position of a supply liquid to a distillation column in the operation termination step in which a solvent is circulated between a reactor and the distillation column, particularly at the time of cleaning after reaction termination, to a position lower than the supply position of a supply liquid to the distillation column in the production operation step, i.e., at the time when the α-olefin low polymer is stably produced. Thus, they have accomplished the present invention based on the findings.

Namely, the gist of the invention is as follows.

[1] A method for producing an α-olefin low polymer, comprising: a production operation step in which an α-olefin that is a raw material is supplied to a reactor and is subjected to a low polymerization reaction in the presence of a catalyst and a solvent and a reaction product containing the α-olefin low polymer that is an objective product is supplied as a supply liquid to a distillation column to purify the product; and an operation termination step in which the supply of the catalyst to the reactor is terminated and the solvent is circulated between the reactor and the distillation column as a supply liquid, wherein the supply position of the supply liquid to the distillation column in the operation termination step is in a position lower than the supply position of the supply liquid to the distillation column in the production operation step.

[2] The method for producing an α-olefin low polymer according to the [1] above, wherein in the operation termination step, after the supply of the catalyst to the reactor is terminated, the supply position of the supply liquid to the distillation column is changed to a position lower than the supply position of the supply liquid to the distillation column in the production operation step.

[3] The method for producing an α-olefin low polymer according to the [1] or [2] above, wherein in the supply liquid to the distillation column in the operation termination step, the concentration of polymers having a molecular weight of 100,000 or more is 100 ppm by weight or more relative to the solvent.

[4] The method for producing an α-olefin low polymer according to any one of the [1] to [3] above, wherein temperature inside the distillation column at the supply position of the supply liquid to the distillation column in the operation termination step is 110° C. or higher.

[5] The method for producing an α-olefin low polymer according to any one of the [1] to [4] above, wherein the operation termination step comprises causing a partial pressure of the α-olefin at a vapor phase part of the reactor to drop in at least two stages.

[6] The method for producing an α-olefin low polymer according to any one of the [1] to [5] above, wherein the operation termination step comprises cleaning at least one of the reactor and a heat exchanger for removing reaction heat.

[7] The method for producing an α-olefin low polymer according to any one of the [1] to [6] above, wherein the supply position of the supply liquid to the distillation column in the operation termination step is a bottom part of the distillation column.

[8] The method for producing an α-olefin low polymer according to any one of the [1] to [7] above, wherein the distillation column contains a high boiling matter separation column.

[9] The method for producing an α-olefin low polymer according to the [8] above, wherein the distillation column further contains an α-olefin separation column and a product separation column.

[10] The method for producing an α-olefin low polymer according to the [8] or [9] above, wherein high-boiling-point components extracted from the column bottom part of the high boiling matter separation column to the high boiling matter tank in the production operation step are supplied and circulated as the supply liquid in the operation termination step to the column bottom part of the high boiling matter separation column.

[11] The method for producing an α-olefin low polymer according to any one of the [1] to [10] above, wherein the α-olefin that is the raw material is ethylene and the α-olefin low polymer that is the objective product is an α-olefin having 4 to 10 carbon atoms.

[12] An apparatus for separating an α-olefin low polymer and polymers from a solution containing the α-olefin low polymer, a solvent, and the polymers, wherein the apparatus has two or more supply ports of the solution at vertically different positions.

[13] The apparatus according to the [12], wherein the position of the supply port nearer to the column top, which is the uppermost supply port of the supply ports, is upper than the lowermost end of trays or filled materials and the position of the supply port nearer to the column bottom, which port is the lowermost supply port of the supply ports, is lower than the lowermost end of the trays or the filled materials.

[14] The apparatus according to the [12] or [13] above, wherein the α-olefin low polymer is a polymerized product of ethylene and is an α-olefin having 4 to 10 carbon atoms.

Effects of Invention

According to the present invention, even when the polymer concentration increases in the termination step of the production operation of an α-olefin low polymer (operation termination step), particularly, during cleaning of the production apparatus, the precipitation of the polymers is suppressed and further, even when the polymers are precipitated, the blockage of the production apparatus is avoided and the operation of the apparatus can be continued.

BRIEF DESCRIPTION OF THE DRAWING

FIG. 1 is a schematic view of showing a production process of 1-hexene of the invention.

MODE FOR CARRYING OUT INVENTION

The following will describe the present invention in detail. Incidentally, the invention is not limited to the following embodiments, and can be carried out with various modifications within a scope of the gist thereof.

1. Production Operation Step

The method for producing an α-olefin low polymer according to the invention comprises a production operation step and an operation termination step.

The production operation step is a step in which an α-olefin that is a raw material is supplied to a reactor and is subjected to a low polymerization reaction in the presence of a catalyst and a solvent and a reaction product containing the α-olefin low polymer that is an objective product is supplied as a supply liquid to a distillation column to purify the product.

The production operation step of the invention is a step of continuously producing the α-olefin low polymer that is the objective product and includes compounds, apparatus, means, operations, conditions, and the like to be described below.

(Raw Material α-Olefin)

In the invention, the α-olefin that is a raw material (hereinafter sometimes referred to simply as "α-olefin", "raw material α-olefin", or "α-olefin that is a monomer") is a linear or branched α-olefin having 2 to 30 carbon atoms, which may be substituted. It is preferably a linear or branched α-olefin having 2 to 6 carbon atoms, which may be substituted, and more preferably a unsubstituted linear α-olefin having 2 to 6 carbon atoms.

Specific examples of such an α-olefin include ethylene, propylene, 1-butene, 1-hexene, 1-octene, 3-methyl-1-butene, and 4-methyl-1-pentene. Of these, ethylene, propylene, and 1-butene are preferred and ethylene is further preferred.

They become poor solvents for deposits (mainly polymers formed by reactions as by-products) accumulated inside the reactor and/or inside a heat exchanger for removing reaction heat.

Moreover, also from the viewpoint that the concentration of the α-olefin can be easily lowered by such a pressure control that the pressure of the reactor is lowered than that at the time of steady operation, as the raw material α-olefin, ethylene, propylene, or 1-butene is preferred and ethylene is further preferred.

In the case where ethylene is used as a raw material, a pure product of ethylene may be used but a raw material mixture containing methane, ethane, acetylene, carbon dioxide, and the like in addition to ethylene can be used. In the case of the raw material mixture is used, the sum of the components other than ethylene is preferably 0.1 mol % or less relative to ethylene. The same shall apply to the other α-olefin.

(α-Olefin Low Polymer)

The α-olefin low polymer in the invention means an oligomer in which several molecules of an α-olefin that is a monomer are bonded. Specifically, it means an oligomer in which 2 to 10 molecules, preferably 2 to 5 molecules of an α-olefin that is a monomer are bonded. Therefore, the α-olefin low polymer in the invention is sometimes referred to as α-olefin oligomer. Similarly, the low polymerization reaction of the α-olefin is sometimes referred to as oligomerization of the α-olefin.

In the case where ethylene is used as a raw material, a substituted or unsubstituted linear or branched α-olefin having 4 to 10 carbon atoms is formed as an objective product and a unsubstituted linear α-olefin having 4 to 10 carbon atoms is preferred. Specifically, there may be mentioned 1-butene that is a dimmer of ethylene, 1-hexene that is a trimer, 1-octene that is a tetramer, 1-decene that is a pentamer, and the like, and 1-hexene is more preferred. In the case where the objective product is 1-hexene, the content of 1-hexene in a mixture of products is preferably 90% by weight or more.

In the case where propylene is used as a raw material, a substituted or unsubstituted linear or branched hexene or nonene having 6 to 9 carbon atoms is formed as an objective product.

In the case where 1-butene is used as a raw material, an octane that is a dimmer of 1-butene is formed as an objective product.

(Catalyst)

The catalyst of the invention is not particularly limited so long as it can oligomerize an α-olefin and can form an α-olefin oligomer, and known and commonly used ones can be employed. Usually, a homogeneous catalyst can be used. As the homogeneous catalyst, preferred is one containing a transition metal-containing compound, an aluminum-containing compound, and a nitrogen-containing compound as catalyst components.

The following will describe suitable embodiments of the catalyst of the invention but the catalyst is not limited thereto.

(Transition Metal-Containing Compound)

The transition metal of the transition metal-containing compound of the invention means one of elements belonging to 3 to 11 groups of the periodic table. Of these, transition metals belonging to 4 to 6 groups of the periodic table are preferred. Specifically, chromium, titanium, zirconium, vanadium, hafnium, and tantalum are more preferred. These transition metals may be used alone or two or more thereof may be used in combination. Further preferred is chromium or titanium and most preferred is chromium.

As the transition metal-containing compound, there may be mentioned a compound represented by the following formula (1):

$$MeZ_n \quad (1)$$

wherein Me represents a transition metal element, Z represents any organic group or inorganic group or an electronegative atom, and n represents an integer of 1 to 6. n is preferably 2 or more and, in that case, Z may be the same or different from each other.

As the organic group, there may be mentioned various groups having 1 to 30 carbon atoms, which may be substituted. Specifically, there may be mentioned a carbonyl group, an alkoxy group, a carboxyl group, a β-diketonate group, a β-ketocarboxyl group, a β-ketoester group, and an amido group. As the inorganic group, metal salt-forming groups such as nitric acid group and sulfuric acid group may be mentioned. As the electronegative atom, oxygen, halogen, and the like may be mentioned. Incidentally, transition metal-containing compounds containing halogen are not included in the halogen-containing compounds to be mentioned later.

In the case of the transition metal-containing compound in which the transition metal is chromium, (hereinafter sometimes referred to as "chromium-containing compound"), specific examples thereof include chromium(IV)-tert-butoxide, chromium(III) acetylacetonate, chromium(III) trifluoroacetylacetonate, chromium(III) hexafluoroacetylacetonate, chromium(III) (2,2,6,6-tetramethyl-3,5-heptanedioate), $Cr(PhCOCHCOPh)_3$ (where Ph represents a phenyl group), chromium(II) acetate, chromium(III) acetate, chromium(III) 2-ethylhexanoate, chromium(III) benzoate, chromium(III) naphthenate, chromium(III) heptanoate, $Cr(CH_3COCHCOOCH_3)_3$, chromous chloride, chromic chloride, chromous bromide, chromic bromide, chromous iodide, chromic iodide, chromous fluoride, and chromic fluoride.

In the case of the transition metal-containing compound in which the transition metal is titanium, (hereinafter sometimes referred to as "titanium-containing compound"), specific examples thereof include $TiCl_4$, $TiBr_4$, $TiI_4$, $TiBrCl_3$, $TiBr_2Cl_2$, $Ti(OC_2H_5)_4$, $Ti(OC_2H_5)_2Cl_2$, $Ti(O-n-C_3H_7)_4$, $Ti(O-n-C_3H_7)_2Cl_2$, $Ti(O-iso-C_3H_7)_4$, $Ti(O-iso-C_3H_7)_2Cl_2$, $Ti(O-n-C_4H_9)_4$, $Ti(O-n-C_4H_9)_2Cl_2$, $Ti(O-iso-C_4H_9)_4$, $Ti(O-iso-C_4H_9)_2Cl_2$, $Ti(O-tert-C_4H_9)_4$, $Ti(O-tert-C_4H_9)_2Cl_2$, $TiCl_4(thf)_2$ (in the chemical formula described in the left, thf represents tetrahydrofuran), $Ti((CH_3)_2N)_4$, $Ti((C_2H_5)_2N)_4$, $Ti((n-C_3H_7)_2N)_4$, $Ti((iso-C_3H_7)_2N)_4$, $Ti((n-C_4H_9)_2N)_4$, $Ti((tert-C_4H_9)_2N)_4$, $Ti(OSO_3CH_3)_4$, $Ti(OSO_3C_2H_5)_4$, $Ti(OSO_3C_3H_7)_4$, $Ti(OSO_3C_4H_9)_4$, $TiCp_2Cl_2$, $TiCp_2ClBr$, $Ti(OCOC_2H_5)_4$, $Ti(OCOC_2H_5)_2Cl_2$, $Ti(OCOC_3H_7)_4$, $Ti(OCOC_3H_7)_2Cl_2$, $Ti(OCOC_3H_7)_4$, $Ti(OCOC_3H_7)_2Cl_2$, $Ti(OCOC_4H_9)_4$, and $Ti(OCOC_4H_9)_2Cl_2$.

In the case of the transition metal-containing compound in which the transition metal is zirconium, (hereinafter sometimes referred to as "zirconium-containing compound"), specific examples thereof include $ZrCl_4$, $ZrBr_4$, $ZrI_4$, $ZrBrCl_3$, $ZrBr_2Cl_2$, $Zr(OC_2H_5)_4$, $Zr(OC_2H_5)_2Cl_2$, $Zr(O-n-C_3H_7)_4$, $Zr(O-n-C_3H_7)_2Cl_2$, $Zr(O-iso-C_3H_7)_4$, $Zr(O-iso-C_3H_7)_2Cl_2$, $Zr(O-n-C_4H_9)_4$, $Zr(O-n-C_4H_9)_2Cl_2$, $Zr(O-iso-C_4H_9)_4$, $Zr(O-iso-C_4H_9)_2Cl_2$, $Zr(O-tert-C_4H_9)_4$, $Zr(O-tert-C_4H_9)_2Cl_2$, $Zr((CH_3)_2N)_4$, $Zr((C_2H_5)_2N)_4$, $Zr((n-C_3H_7)_2N)_4$, $Zr((iso-C_3H_7)_2N)_4$, $Zr((n-C_4H_9)_2N)_4$, $Zr((tert-C_4H_9)_2N)_4$, $Zr(OSO_3CH_3)_4$, $Zr(OSO_3C_2H_5)_4$, $Zr(OSO_3C_3H_7)_4$, $Zr(OSO_3C_4H_9)_4$, $ZrCp_2Cl_2$, $ZrCp_2ClBr$, $Zr(OCOC_2H_5)_4$, $Zr(OCOC_2H_5)_2Cl_2$, $Zr(OCOC_3H_7)_4$, $Zr(OCOC_3H_7)_2Cl_2$, $Zr(OCOC_3H_7)_4$, $Zr(OCOC_3H_7)_2Cl_2$, $Zr(OCOC_4H_9)_4$, $Zr(OCOC_4H_9)_2Cl_2$, $ZrCl_2(HCOCFCOF)_2$, and $ZrCl_2(CH_3COCFCOCH_3)_2$.

In the case of the transition metal-containing compound in which the transition metal is hafnium, (hereinafter sometimes referred to as "hafnium-containing compound"), specific examples thereof include dimethylsilylenebis{1-(2-methyl-4-isopropyl-4H-azulenyl)}hafnium dichloride, dimethylsilylenebis{1-(2-methyl-4-phenyl-4H-azulenyl)}hafnium dichloride, dimethylsilylenebis[1-{2-methyl-4-(4-chlorophenyl)-4H-azulenyl}]hafnium dichloride, dimethylsilylenebis[1-{2-methyl-4-(4-fluorophenyl)-4H-azulenyl}]hafnium dichloride, dimethylsilylenebis[1-{2-methyl-4-(3-chlorophenyl)-4H-azulenyl}]hafnium dichloride, dimethylsilylenebis[1-{2-methyl-4-(2,6-dimethylphenyl)-4H-azulenyl}]hafnium dichloride, dimethylsilylenebis{1-(2-methyl-4,6-diisopropyl-4H-azulenyl)}hafnium dichloride, diphenylsilylenebis{1-(2-methyl-4- phenyl-4H-azulenyl)}hafnium dichloride, methylphenylsilylenebis{1-(2-methyl-4-phenyl-4H-azulenyl)}hafnium dichloride, methylphenylsilylenebis[1-{2-methyl-4-(1-naphthyl)-4H-azulenyl}]hafnium dichloride, dimethylsilylenebis{1-(2-ethyl-4-phenyl-4H-azulenyl)}hafnium dichloride, dimethylsilylenebis[1-{2-ethyl-4-(1-anthracenyl)-4H-azulenyl}]hafnium dichloride, dimethylsilylenebis[1-{2-ethyl-4-(2-anthracenyl)-4H-azulenyl}] hafnium dichloride, dimethylsilylenebis[1-{2-ethyl-4-(9-phenanthryl)-4H-azulenyl}]hafnium dichloride, dimethylmethylenebis[1-{2-methyl-4-(4-biphenylyl)-4H-azulenyl}]hafnium dichloride, dimethylgermylenebis[1-{2-methyl-4-(4-biphenylyl)-4H-azulenyl}]hafnium dichloride, dimethylsilylenebis[1-{2-ethyl-4-(3,5-dimethyl-4-trimethylsilylphenyl)-4H-azulenyl}]hafnium dichloride, dimethylsilylene[1-{2-methyl-4-(4-biphenylyl)-4H-azulenyl}][1-{2-methyl-4-(4-biphenylyl)indenyl}]hafnium dichloride, dimethylsilylene {1-(2-ethyl-4-phenyl-4H-azulenye}{1-(2-methyl-4,5-benzoindenyl)}hafnium dichloride, dimethylsilylenebis{1-(2-methyl-4-phenylindenyl)}hafnium dichloride, dimethylsilylenebis{1-(2-methyl-4,5-benzoindenyl)}hafnium dichloride, and dimethylsilylenebis[1-{2-methyl-4-(1-naphthyl)indenyl}]hafnium dichloride.

Of these transition metal-containing compounds, chromium-containing compounds are preferred and, of the chromium-containing compounds, particularly preferred is chromium(III) 2-ethylhexanoate.

(Aluminum-Containing Compound)

As the aluminum-containing compound of the invention, for example, there may be mentioned a trialkylaluminum compound, an alkoxyalkylaluminum compound, or a hydrogenated alkylaluminum compound.

The trialkylaluminum compound has alkyl groups having 1 to 8 carbon atoms and the alkyl groups may be the same or different from each other. For example, trimethylaluminum, triethylaluminum, and triisobutylaluminum may be mentioned.

The alkoxyalkylaluminum compound has alkyl groups having 1 to 8 carbon atoms and an alkoxy group having 1 to 8 carbon atoms, and specific examples thereof include diethylaluminum ethoxide and the like.

The hydrogenated alkylaluminum compound has alkyl groups having 1 to 8 carbon atoms and hydrogen and specific examples thereof include diethylaluminum hydride and the like.

Of these, trialkylaluminum compound is preferred and particularly, triethylaluminum is further preferred. These compounds may be used as a single compound or may be used as a mixture of a plurality of the compounds.

(Nitrogen-Containing Compound)

As the nitrogen-containing compound of the invention, an amine compound, an amide compound, or an imide compound may be mentioned.

As the amine compound, for example, a pyrrole compound may be mentioned. Specific examples thereof include pyrrole, 2,4-dimethylpyrrole, 2,5-dimethylpyrrole, 2-methyl-5-ethylpyrrole, 2,5-dimethyl-3-ethylpyrrole, 3,4-dimethylpyrrole, 3,4-dichloropyrrole, 2,3,4,5-tetrachloropyrrole, 2-acetylpyrrole, 2-methyl-4-isopropylpyrrole, 2,5-diethylpyrrole, 2,5-dibenzylpyrrole, 2,5-diisopropylpyrrole, and a dipyrrole having two pyrrole rings bonded through a substituent, and derivatives thereof. Examples of the derivatives include metal pyrrolide derivatives. Specific examples thereof include aluminum pyrrolides such as diethylaluminum pyrrolide, ethylaluminum dipyrrolide, aluminum tripyrrolide, diethylaluminum (2,5-dimethylpyrrolide), ethylaluminum bis(2,5-dimethylpyrrolide), and aluminum tris (2,5-dimethyl-pyrrolide), sodium pyrrolides such as sodium pyrrolide and sodium (2,5-dimethylpyrrolide), lithium pyrrolides such as lithium pyrrolide and lithium (2,5-dimethylpyrrolide), and potassium pyrrolides such as potassium pyrrolide and potassium (2,5-dimethylpyrrolide). Incidentally, the aluminum pyrrolides are not included in the aforementioned aluminum-containing compound. Furthermore, the halogen-containing pyrrole compound is not included in the halogen-containing compound to be mentioned below.

Examples of the amide compound include acetamide, N-methylhexanamide, succinamide, maleamide, N-methylbenzamide, imidazole-2-carboxamide, di-2-thenoylamine, β-lactam, δ-lactam, and ε-caprolactam, or salts of them with a metal belonging to 1, 2, or 13 group of the periodic table.

Examples of the imide compound include 1,2-cyclohexanedicarboxyimide, succinimide, phthalimide, maleimide, 2,4,6-piperidinetrione, and perhydroazecine-2,10-dione, or salts of them with a metal belonging to 1, 2, or 13 group of the periodic table. Examples of sulfonamides and sulfonimides include benzenesulfonamide, N-methylmethanesulfonamide, and N-methyltrifluoromethylsulfonamide, or salts of them with a metal belonging to 1, 2, or 13 group of the periodic table. These compounds may be used as a single compound or may be used as a plurality of the compounds.

In the invention, of these, an amine is preferred. In particular, a pyrrole compound is more preferred and particularly preferred is 2,5-dimethylpyrrole or diethylaluminum (2,5-dimethylpyrrolide).

Moreover, in the case of using a homogeneous catalyst in the invention, in addition to the three components of the aforementioned transition metal-containing compound, aluminum-containing compound, and nitrogen-containing compound, it is more preferred to further contain a halogen-containing compound.

As the halogen-containing compound, there may be mentioned a halogenated alkylaluminum compound, a benzyl chloride skeleton-containing compound, a linear halogenated hydrocarbon having 1 or more carbon atoms and having 2 or more halogen atoms, and a cyclic halogenated hydrocarbon having 3 or more carbon atoms and having 2 or more halogen atoms. The halogenated alkylaluminum compound is not included in the aluminum-containing compound. Examples include diethylaluminum chloride, ethylaluminum sesquichloride, benzyl chloride, (1-chloroethyl)benzene, 2-methylbenzyl chloride, 3-methylbenzyl chloride, 4-methylbenzyl chloride, 4-ethylbenzyl chloride, 4-isopropylbenzyl chloride, 4-tert-butylbenzyl chloride, 4-vinylbenzyl chloride, α-ethyl-4-methylbenzyl chloride, α,α'-dichloro-o-xylene, α,α'-dichloro-m-xylene, α,α'-dichloro-p-xylene, 2,4-dimethylbenzyl chloride, 2,5-dimethylbenzyl chloride, 2,6-dimethylbenzyl chloride, 3,4-dimethylbenzyl chloride, 2,3,5,6-tetramethylbenzyl chloride, 1-(chloromethyl)naphthalene, 1-(chloromethyl)-2-methylnaphthalene, 1,4-bis-chloromethyl-2,3-dimethylnaphthalene, 1,8-bis-chloromethyl-2,3,4,5,6,7-hexamethylnaphthalene, 9-(chloromethyl)anthracene, 9,10-bis(chloromethyl)anthracene, 7-(chloromethyl)benzanthracene, 7-chloromethyl-12-methylbenzanthracene, carbon tetrachloride, 1,1,1-trichloroethane, 1,1,2,2-tetrachloroethane, pentachloroethane, hexachloroethane, 1,2,3-trichlorocyclopropane, 1,2,3,4,5,6-hexachlorocyclohexane, and 1,4-bis(trichloromethyl)-2,3,5,6-tetrachlorobenzene.

(Method for Contact)

In the invention, in the case where the catalyst to be used for the low polymerization (oligomerization) reaction is a three-component catalyst containing the aforementioned transition metal-containing compound, aluminum-containing compound, and nitrogen-containing compound or a four-component catalyst further containing the halogen-containing compound, it is preferred to bring the raw material α-olefin into contact with the catalyst in a mode where the transition metal-containing compound does not come into contact with the aluminum-containing compound beforehand or a time of previous contact is short. By adopting such a contact mode, the low polymerization (oligomerization) reaction of the raw material α-olefin can be selectively carried out and the oligomer of the raw material α-olefin can be obtained in high yields. In the invention, the "mode where the transition metal-containing compound does not come into contact with the aluminum-containing compound beforehand or a time of previous contact is short" Means that the above mode is maintained not only at the starting time of the reaction but also at the time when the raw material α-olefin and respective catalyst components are then additionally supplied to the reactor.

The reason why the activity of the low polymerization reaction of the α-olefin decreases in the case where the catalyst is used in the mode where the transition metal-containing compound comes into contact with the aluminum-containing compound beforehand is not yet clear but is presumed as follows.

For example, in the case where the transition metal-containing compound is brought into contact with an alkylaluminum compound, it is considered that a ligand exchange reaction proceeds between the ligand coordinating to the transition metal-containing compound and the alkyl group in the alkylaluminum compound and thus the catalyst becomes unstable. For the reason, a decomposition and reduction reaction of an alkyl-transition metal-containing compound predominantly proceeds and as a result, metalization unsuitable for the low polymerization reaction of the α-olefin occurs and the activity of the low polymerization reaction of the α-olefin decreases.

Therefore, in the case where the catalyst is composed of the above four components, i.e., the transition metal-containing compound (a), the nitrogen-containing compound (b), the aluminum-containing compound (c), and the halogen-containing compound (d), the mode for contact of the components is performed, usually in the presence of the α-olefin by, for example, (1) a method of introducing a solution containing the catalyst components (b), (c), and (d) and a solution containing the catalyst component (a) into the reactor, respectively, (2) a method of introducing a solution containing the catalyst components (a), (b), and (d) and a solution containing the catalyst component (c) into the reactor, respectively, (3) a method of introducing a solution containing the catalyst components (a) and (d) and a solution containing the catalyst components (b) and (c) into the reactor, respectively, (4) a method of introducing a solution containing the catalyst components (c) and (d) and a solution containing the catalyst components (a) and (b) into the reactor, respectively, (5) a method of introducing a solution containing the catalyst components (a) and (b) and a solution containing the catalyst components (c) and (d) into the reactor, respectively, (6) a method of introducing a solution containing the catalyst components (b) and (c) and a solution containing the catalyst components (a) and (d) into the reactor, respectively, (7) a method of introducing a solution containing the catalyst component (c) and a solution containing the catalyst components (a), (b), and (d) into the reactor, respectively, (8) a method of introducing a solution containing the catalyst component (a) and a solution containing the catalyst components (b) to (d) into the reactor, respectively, and (9) a method of simultaneously and independently introducing each of the catalyst components (a) to (d) into the reactor. The above each solution is usually prepared using the solvent to be used in the reaction.

(Solvent)

The solvent for the invention is not particularly limited but saturated hydrocarbons are suitably used. Preferably, for example, the solvent is a linear saturated hydrocarbon having 4 to 20 carbon atoms or an alicyclic saturated hydrocarbon having 4 to 20 carbon atoms, such as butane, pentane, 3-methylpentane, n-hexane, n-heptane, 2-methylhexane, octane, cyclohexane, methylcyclohexane, 2,2,4-trimethylpentane, or decalin. In addition, there may be used an aromatic hydrocarbon such as benzene, toluene, xylene, ethylbenzene, mesitylene, or tetralin or an α-olefin oligomer such as 1-hexene, 1-octene, or 1-decene, as a solvent. They can be used alone or can be also used as a mixed solvent.

Of these solvents, it is preferred to use a linear saturated hydrocarbon or alicyclic saturated hydrocarbon having 7 to 10 carbon atoms form the viewpoints that formation or precipitation of by-product polymers such as polyethylene can be suppressed and further, high catalyst activity tends to be obtained. Specifically, n-heptane or cyclohexane is more preferred and most preferred is n-heptane.

(Conditions for Low Polymerization (Oligomerization) Reaction)

In the invention, in the case where a homogeneous catalyst is used as the catalyst and is a three-component catalyst containing the aforementioned transition metal-containing compound, aluminum-containing compound, and nitrogen-containing compound or a four-component catalyst further containing the halogen-containing compound, with regard to the ratio of each constituting component, usually, relative to 1 mol of the transition metal-containing compound, the aluminum-containing compound is 1 mol or more, preferably 10 mol or more and 200 mol or less, preferably 150 mol or less and the nitrogen-containing compound is 1 mol or more and 50 mol or less, preferably 30 mol or less. The halogen-containing compound is 1 mol or more, preferably 3 mol or more and 60 mol or less, preferably 40 mol or less.

In the invention, the amount of the catalyst to be used is not particularly limited but, in the case where the catalyst is a three-component catalyst containing the aforementioned transition metal-containing compound, aluminum-containing compound, and nitrogen-containing compound or a four-component catalyst further containing the halogen-containing compound, the amount is usually an amount so as to be $1.0 \times 10^{-8}$ mol to 0.05 mol, preferably $5.0 \times 10^{-8}$ mol to 0.02 mol, and further preferably $1.0 \times 10^{-7}$ mol to 0.005 mol in terms of 1 atom of the transition metal of the transition metal-containing compound, per 1 liter of the solvent.

In the invention, the reaction temperature of the low polymerization reaction is not particularly limited but is usually from 0 to 250° C., preferably from 50 to 200° C., and further preferably from 80 to 170° C.

Moreover, the reaction pressure is in a range of usually from normal pressure (0) to 25 MPaG (gauge pressure, the same shall apply hereinafter), preferably from 0.5 to 15 MPaG, and further preferably from 1 to 10 MPaG. The partial pressure of the raw material α-olefin is not particularly limited but is in a range of usually from normal pressure to 23 MPaG, preferably from 0.4 to 14 MPaG, and further preferably from 0.9 to 9.3 MPaG.

Furthermore, the residential time in the reactor is not particularly limited but is in a range of usually from 1 minute to 10 hours, preferably from 5 minutes to 3 hours, and further preferably from 10 minutes to 1 hour.

The reaction type may be any of a batch type, a semi-batch type, and a continuous type.

(Method for Producing α-Olefin Low Polymer)

The method for producing the α-olefin low polymer will be described below by referring to an example of low polymerization to 1-hexene that is a trimer of ethylene as an α-olefin low polymer using ethylene as an α-olefin. However, the α-olefin is not limited to ethylene and the α-olefin low polymer is not limited to 1-hexene and the following production method is applicable to the case where the above-described α-olefin low polymer is produced using the above-described α-olefin of the invention.

FIG. 1 is a production flow of 1-hexene using ethylene as a raw material. FIG. 1 shows a completely mixing and stirring type reactor 10 in which ethylene is subjected to low polymerization in the presence of a catalyst, a degassing tank 20 that separates an unreacted ethylene gas from a reaction liquid extracted from the reactor 10, an ethylene separation column 30 that distills ethylene in the reaction liquid extracted from the degassing tank 20, a high boiling matter separation column 40 that separates a high-boiling-point substance in the reaction liquid extracted from the ethylene separation column 30, and a 1-hexene separation column 50 that conducts distillation of the reaction liquid extracted from the column top of the high boiling matter separation column 40 to distill 1-hexene. Furthermore, a compressor 17 that circulates the unreacted ethylene separated in the degassing tank 20 and a condenser 16 into the reactor 10 via a circulation piping 21 is provided.

The reactor 10 in FIG. 1 is a conventionally well-known type one equipped with a stirring machine 10a, a baffle, a jacket, and the like. Beside, as the reactor, a loop reactor or the like may be used. The stirring machine 10a is a paddle type one but, besides, a stirring blade of the type such as Pfaudler, propeller, turbine, or the like may be used in combination with a baffle such as a planar plate, a cylinder, or a hairpin coil.

Ethylene is continuously supplied to the reactor 10 from an ethylene supply piping 12a via the compressor 17 and a first supply piping 12. Here, in the case where the compressor 17 is, for example, a two-stage compression system, the first stage is connected onto a circulation piping 31, and the second stage is connected after a circulation pipings 21 and 31 and the ethyle supply piping 12a are combined, thereby making it possible to reduce electricity consumption.

Furthermore, a solvent, n-heptane, to be used in the low polymerization reaction of ethylene is supplied to the reactor 10 from a second supply piping 13.

The transition metal-containing compound and the nitrogen-containing compound are prepared in catalyst tanks (not shown in the FIGURE) beforehand and are supplied to the reactor 10 from the second supply piping 13 via a catalyst supply piping 13a.

The aluminum-containing compound is usually supplied from a third supply piping 14 but, when a time until it is supplied to the reactor falls within several minutes after the contact with the transition metal-containing compound, it may be supplied to the reactor 10 via the second supply piping 13.

The halogen-containing compound is usually supplied from a fourth supply piping 15 but may be supplied to the reactor 10 via the second supply piping 13.

For the purpose that a uniform mixture of each catalyst component can be supplied to the reactor 10 and stirring power of the reactor 10 is reduced, a static mixer or the like may be provided between the second supply piping 13 and the reactor 10.

The trimerization reaction of ethylene is preferably conducted such that a molar ratio of 1-hexene to ethylene in the reaction liquid ((molar concentration of 1-hexene in reaction liquid)/(molar concentration of ethylene in reaction liquid)) becomes from 0.05 to 1.5, and particularly from 0.10 to 1.0. That is, it is preferred that in the case of a continuous reaction, a catalyst concentration, reaction pressure, and other conditions are controlled such that the molar ratio of 1-hexene to ethylene in the reaction liquid falls within the above range. In the case of a batch reaction, the trimerization reaction of ethylene is preferably stopped at the time when the molar ratio falls within the above range. As a result, by-production of components having a boiling point higher than that of 1-hexene is suppressed and thereby selectivity of 1-hexene is further increased.

The reaction liquid continuously extracted from the bottom of the reactor 10 via a piping 11 is subjected to reaction termination by the action of a deactivator supplied from a deactivator supply piping 11a, and is supplied to the degassing tank 20. The reaction liquid from which unreacted ethylene has been degassed is extracted from the bottom of the degassing tank 20. Operation conditions of the degassing tank 20 are not particularly limited but the temperature is usually from 0° C. to 240° C., and preferably from 50° C. to 190° C., and the pressure is not particularly limited but is usually from normal pressures to 14 MPaG, and preferably from normal pressures to 9 MPaG.

The reaction liquid from which unreacted ethylene gas has been degassed in the degassing tank 20 is extracted from the bottom of the degassing tank 20, and supplied to the ethylene separation column 30 by a piping 22. In the ethylene separation column 30, ethylene is distilled from the column top by distillation, and circulated and supplied to the reactor 10 via the circulation piping 31 and the first supply piping 12. The reaction liquid from which ethylene has been removed is extracted from the column bottom. Incidentally, as a supply piping to the ethylene separation column, in addition to the piping 22, a piping capable of supply to a position at which a distillation column internal temperature is higher than the case of the piping 22 may be provided.

Operation conditions of the ethylene separation column 30 are that the column top pressure is not particularly limited but usually from normal pressures to 3 MPaG, and preferably from normal pressures to 2 MPaG, the reflux ratio (R/D) is generally from 0 to 500, and preferably from 0.1 to 100, and the temperature of the supply plate is usually from 80° C. to 170° C.

Then, the reaction product (also referred to as reaction liquid) containing the α-olefin low polymer that is the objective product after ethylene has been distilled in the ethylene separation column 30 is extracted from the column bottom of the ethylene separation column 30, and is supplied to the high boiling matter separation column 40 by a piping 32 and purified. As the distillation column of the invention, the high boiling matter separation column 40 is suitably exemplified.

In the high boiling matter separation column 40, a low-boiling-point components (1-hexene as the objective product, n-heptane as the solvent) are distilled from the column top by distillation via a piping 41. Moreover, high-boiling-point components (high boiling matter, deactivated catalyst) are extracted from the column bottom via a piping 42. The high-boiling-point components extracted from the piping 42 are transferred to a high boiling matter tank (not shown in the FIGURE). In the high-boiling-point components, an alcohol or amine having 6 or more carbon atoms is preferably present in a free state since it can deactivate a minute amount of the catalyst components such as an alkylaluminum contained in the polymers.

Operation conditions of the high boiling matter separation column 40 are that the column top pressure is usually not particularly limited but is usually from normal pressure to 1 MPaG, and preferably from normal pressure to 0.5 MPaG, the reflux ratio (R/D) is not particularly limited but is usually from 0 to 100, and preferably from 0.1 to 20, and the temperature of the supply plate (supply plate of the piping 32) is usually from 60° C. to 105° C.

The distillate from the column top of the high boiling matter separation column 40 is supplied to a 1-hexene separation column 50 by the piping 41. In the 1-hexene separation column 50, 1-hexene is distilled by distillation from a piping 51 at the column top. Moreover, n-heptane that is the solvent is extracted from the column bottom of the 1-hexene separation column 50 via a solvent circulation piping 52, and with by-passing a solvent drum 60, is further circulated and supplied as a reaction solvent to the reactor 10 via the second supply piping 13.

Operation conditions of the 1-hexene separation column 50 are not particularly limited but are that the column top pressure is usually from normal pressure to 1 MPaG, and preferably from normal pressure to 0.5 MPaG, and the reflux ratio (R/D) is usually from 0 to 100, and preferably from 0.1 to 20.

(High Boiling Matter)

The high boiling matter is one having a boiling point higher than that of the objective product, of α-olefin lower polymer, and particularly, one having a molecular weight of 10,000 is called a polymer. For example, in the case where the α-olefin is ethylene and the objective product is 1-hexene, an α-olefin low polymer having more than 6 carbon atoms is high boiling matter and, in this case, decenes become main components.

2. Operation Termination Step

The operation termination step of the invention includes that the supply of the catalyst to the reactor is terminated and the solvent is supplied and circulated between the reactor and the distillation column as a supply liquid, and the supply liquid is supplied to the distillation column from a position lower than the supply position of the supply liquid to the distillation column in the production operation step.

Here, the supply of the catalyst to the reactor may be supply of the catalyst to the reactor after the catalyst is formed outside the reactor beforehand or may be formation of an active species of the catalyst in the reactor. Therefore, the termination of the supply of the catalyst to the reactor may be termination of the supply of the catalyst or may be termination of the supply of the above-described compounds that form the catalyst.

The supply and circulation of the solvent between the reactor and the distillation column, means a supply and circulation of the solvent after a separation of reaction product in the distillation column.

Moreover, the circulation of the solvent between the reactor and the distillation column is circulation of the solvent between the ethylene separation column, the high boiling matter separation column, or the objective product (1-hexene) separation column and the reactor when the step is the above-described production operation step. Of these separation columns, the high boiling matter separation column is preferred but the solvent may be circulated to the other separation column(s) in addition to the high boiling matter separation column and further it is more preferred to provide the α-olefin separation column and the product separation column.

Furthermore, the position lower than the supply position of the supply liquid to the distillation column in the production operation step is a position nearer to the column bottom than the supply position of the supply liquid to the distillation column in the production operation step. That is, it is sufficient that the supply position of the supply liquid to the distillation column in the operation termination step is located by one or more of theoretical plates (about 0.5 m or more), more preferably two or more of theoretical plates (about 1.0 m or more) lower than the supply position in the production operation step.

Such a distillation column is preferably an apparatus that separates the α-olefin low polymer and the polymers from the solution containing the α-olefin low polymer, the solvent, and the polymers and is preferably a high boiling matter separation column in the production operation step. The distillation column is an apparatus having two or more supply ports of the solution at vertically different parts, i.e., supply port(s) nearer to the column top and supply port(s) nearer to the column bottom.

Moreover, it is more preferred that the position of the supply port nearer to the column top, which port is the uppermost feed port, is upper than the lowermost end of trays or filled materials and the position of the supply port nearer to the column bottom, which port is the lowermost feed port, is lower than the lowermost end of the trays or the filled materials.

Furthermore, suitably, the operation termination step of the invention includes causing a partial pressure of the α-olefin at the vapor phase part of the reactor to drop in at least two stages and cleaning of the reactor and/or the heat exchanger for removing reaction heat.

As the termination method of the catalyst supply to the reactor, for example, in FIG. 1, the supply of the transition metal-containing compound and the nitrogen-containing compound from the catalyst supply piping 13a, the supply of the aluminum-containing compound from the third supply piping 14, and the supply of the halogen-containing compound from the fourth supply piping 15 are terminated. When the supply of the catalyst to the reactor is terminated, the catalyst active species decreases and gradually the reaction is terminated.

In the invention, even after the supply of the catalyst to the reactor is terminated, the solvent circulation in the production operation step is continued. The circulation amount of the solvent circulation may be increased or decreased.

Simultaneously to the termination of the reaction, the supply of the raw material α-olefin is also decreased. That is, the partial pressure of the α-olefin at the vapor phase part of the reactor is dropped. When the solvent circulation is continued in this state, the polymer concentration in the solvent increases. The reason is not clear but the present inventors consider as follows.

Namely, solid matter is produced as a by-product by the low polymerization (oligomerization) reaction of the α-olefin. The solid matter is one containing the polymers and the residue of the catalyst supplied to the reactor and the matter precipitates when it cannot be dissolved in the solvent and adheres to inner walls of production equipments such as the reactor, the heat exchanger, and the distillation column. Moreover, it is also considered that the catalyst supplied to the reactor or the residue thereof remain at a liquid-side boundary film part present at a solid-liquid phase boundary of the inner wall part of the reactor and thereby polymers form and grow at the inner wall part of the reactor. Incidentally, when the solid matter adhered to the inner walls of the production equipments grows or the precipitated solid matter deposits, the production equipments may be sometimes blocked.

When the α-olefin concentration in the solvent is kept high, the α-olefin acts as a poor solvent to the solid matter, so that the solid matter is prevented from being solved in the solvent. Moreover, when the low polymerization reaction of the α-olefin is terminated, the concentration of the α-olefin oligomer that becomes a poor solvent to the solid matter (polymers) in the solvent decreases, so that the solid matter is likely to be dissolved in the solvent.

When the polymer concentration in the solvent increases, the trays, downcomer, or filled materials of the distillation column may be sometimes blocked by the polymers precipitated due to temperature drop after the passage through a valve that controls the flow rate of a liquid to be supplied to the distillation column (particularly the high boiling matter separation column).

As the polymer concentration in the solvent to be supplied to the distillation column, it is desirable that the concentration of polymers having a molecular weight of 100,000 or more is controlled to preferably 1,500 ppm by weight or less, more preferably 1,000 ppm by weight or less. When the polymer concentration is exceedingly too high, the polymers precipitated due to the temperature drop after the passage through a valve that controls the flow rate of a liquid to be supplied to the distillation column increases to a large amount and hence there is a risk of piping blockage. When the polymer concentration in the solvent increases, by changing the supply position of the supply liquid to the distillation column to a position lower than the supply position in the production operation step, the precipitation of the solid matter can be suppressed or the blockage of the apparatus can be prevented even when the solid matter is precipitated.

The mode for changing the supply position of the supply liquid to the distillation column to the lower position is not particularly limited and examples thereof include a mode of switching a line from an upper line to a lower line and a mode of decreasing the supply amount from the upper line and increasing the supply amount from the lower line. In FIG. 1, for example, as a supply piping to the high boiling matter separation column 40, other than the piping 32, a piping 33 for supply to a distillation column higher temperature part than the piping 32 is present. Since the distillation column has usually a re-boiler at the column bottom, the piping 33 is located lower than the piping 32. When the piping 33 is used, in the case where the polymer concentration in the reaction liquid extracted from the ethylene separation column 30 increases, it becomes possible to perform operation for preventing the blockage of the high boiling matter separation column 40.

The timing of changing the supply position of the supply liquid to the distillation column to the lower position is not particularly limited so long as the change is carried out within the operation termination step. For example, the change may be conducted simultaneously to the termination of the catalyst supply to the reactor, may be conducted after the termination of the catalyst supply, or may be conducted even before the termination of the catalyst supply since the timing is included in the operation termination step and hence the catalyst supply may be terminated shortly.

Moreover, the inventors have found that the possibility of occurrence of the above problem such as a risk of piping blockage due to an increase of the precipitated polymers to a large amount, increases in the case where the concentration of the polymers having a molecular weight of 100,000 or more in the supply liquid to the distillation column is 100 ppm by weight or more. In other word, when a solution containing the polymers having a molecular weight of 100,000 or more in an amount of 100 ppm by weight or more is supplied to the distillation column, the solvent is flushed by pressure drop at the supply part of the distillation column after the passage through the valve that controls the liquid flow rate and, at the time of temperature drop, the polymers are precipitated under fluidizing and stirring conditions and thereby large-sized polymers are precipitated, so that the distillation column may cause flooding in some cases. It is considered that this is because the liquid becomes difficult to drop from the downcomer of the supply plate by the deposition of the lump-shaped polymer deposits deposit at the downcomer part of the supply plate. The reason for the precipitation of the large-sized polymers is not clear but it is considered that, in the case where polymers having a large molecular weight are present in a certain concentration or more under fluidizing or stirring conditions, the polymers become string-shaped or lump-shaped large sized ones by complicatedly entangling individual polymer molecules at the time of precipitation. In the case of polymers having a molecular weight of less than 100,000, since the molecular chain is short, it is considered that the polymer molecule chains are less likely to be entangled each other.

Therefore, in the present invention, it is preferred to change the supply position of the supply liquid to the distillation column to the lower position before the concentration of the polymers having a molecular weight of 100,000 or more in the supply liquid to the distillation column becomes 100 ppm by weight. In other word, the effect of the invention by changing the supply position of the supply liquid to the distillation column in the operation termination step to a position lower than the supply position of the supply liquid to the distillation column in the production operation step, becomes marked in a case of using the supply liquid where the concentration of the polymers having a molecular weight of 100,000 or more is 100 ppm by weight or more. Incidentally, this phenomenon may occur in common not only in the case where the raw material α-olefin is ethylene but also in the raw material α-olefins defined in the invention.

The column internal temperature at the supply position of the supply liquid to the distillation column is preferably a temperature of 110° C. or higher which is a temperature where the polymers are swollen, adhesiveness and hardness decrease, and the polymer solubility increases, and further preferably a temperature of 130° C. or higher which is the melting point of the polymers. An upper limit of the column internal liquid temperature at the liquid supply position to the distillation column is not particularly limited but may be usually coincident with a preferable upper limit of the reaction temperature.

As the supply position of the supply liquid to the distillation column in the operation termination step is preferably a column bottom part having no tray or filled material. That is, the distillation column is roughly classified into a filled column and a tray column according to the inner structure. In the filled column, filled materials are incorporated, and distillation is achieved by gas-liquid contact on the surface of the filled materials. In the tray column, a plurality of plates having open holes, called trays, are installed, and distillation is achieved by gas-liquid contact on the trays.

The bottom part of the distillation column means a position lower than the filled material or tray present at the lowermost end of the plurality of filled materials or trays installed in these distillation columns.

As the dropping method of the partial pressure of the α-olefin at the vapor phase part of the reactor, the pressure is dropped preferably in two stages, more preferably in three stages. That is, it is preferred to drop the partial pressure of the α-olefin little by little stepwise. Thereby, an effect of polymer blockage prevention at low-temperature piping parts is obtained. The pressure of the α-olefin in the operation termination step is from 0% to 99%, preferably from 1% to 75% of the pressure of the raw material α-olefin in the production operation step (at the time of the reaction). In the case where the raw material α-olefin is ethylene and the α-olefin low polymer is 1-hexene, the pressure is further preferably from 10% to 45% of the pressure of the raw material α-olefin at the time of the reaction.

As the dropping rate of the partial pressure of the α-olefin, for example, the ethylene supply amount from the first supply piping in FIG. 1 is reduced and the pressure of the reactor is reduced from 7 MPaG to 3 MPaG. The reducing rate is usually 10 minutes or more, preferably 30 minutes or more, and further preferably 60 minutes or more per 1 MPa.

In the operation termination step of the invention, the supply position of the supply liquid to the distillation column is made lower than that in the production operation step but in the distillation column, the objective product is distilled from the column and high boiling matter is discharged from the bottom. In the production operation step, the bottom product is preferably stored in the high boiling matter tank, and in the operation termination step, the bottom product is preferably circulated between the distillation column and the high boiling matter tank. This is because, since the polymer concentration of the supply liquid to be supplied to the distillation column in the operation termination step increases, the above operation results in dilution with the bottom product having a polymer concentration lower than that in the supply liquid and coming from the high boiling matter tank having a volume much larger than that of the distillation column bottom part, and thus contributes the blockage prevention.

In FIG. 1, the high-boiling-point components are extracted from the column bottom part of the high boiling matter separation column 40 via the piping 42 and is transferred to the high boiling matter tank (not shown in the FIGURE). As for the high-boiling-point components stored in the high boiling matter tank, in order to prevent the blockage of the piping and devices at the time when the polymer concentration at the column bottom part of the high boiling matter separation column 40 becomes high, it is preferred to provide an equipment for supplying and circulating a certain amount of the components to the column bottom part of the high boiling matter separation column 40. Furthermore, there is also an effect that an decrease in heat transfer coefficient of the re-boiler of the distillation column is prevented by decreasing a highly viscose polymer liquid to low viscosity and thus solvent loss owing to no boiling of the solvent is prevented.

(Cleaning of Production Equipments)

In the operation termination step of the invention, it is preferred to carry out cleaning of the production equipments. The cleaning means removal of the solid matter adhered, deposited, grown on the places through which process fluids pass, for example, inner walls and the like of the reactor, incidental equipments of the reactor, and the heat exchanger for removing reaction heat, and the like, by dissolving or swelling the matter with a solvent, and further may include discharge of the solid matter from the process system.

The solid matter adhered to the vapor phase part of the reactor and the like may be dissolved in the solvent after the solid matter is stripped off from the inner walls of the equipments by directly injecting the solvent to the matter beforehand at the time of dissolution in the solvent.

With referring to an example of low polymerization (oligomerization) to 1-hexene that is a trimer of ethylene as the α-olefin oligomer using ethylene as the α-olefin, the method for cleaning the production equipments of the α-olefin oligomer will be described. The α-olefin is not limited to ethylene and the α-olefin oligomer is not limited to 1-hexene, and the following cleaning method may be also applied to the case where the other α-olefin is used as the raw material or the other α-olefin oligomer is produced.

The cleaning of the reactor and the like is performed by circulating the solvent in the order of the reactor 10, the piping 11, the degassing tank 20, the piping 22, the ethylene separation column 30, the piping 33, the high boiling matter separation column 40, the piping 41, the 1-hexene separation column 50, the solvent circulation piping 52, and the second supply piping 13, dissolving the polymers adhered mainly to the reactor 10 in the solvent, and extracting the polymers dissolved in the solvent from the piping 42 of the bottom part of the high boiling matter separation column 40.

Moreover, as the cleaning operation of the heat exchanger for removing reaction heat, for example, there may be mentioned an operation of introducing the solvent from a lower nozzle and extracting it from an upper nozzle or an operation of introducing the solvent from a spray nozzle and extracting it from a lower nozzle. In this method, cleaning can be performed without opening the reactor after the low polymerization (oligomerization) reaction of the α-olefin is terminated, so that the method is preferred since various works involved in the equipment opening can be omitted and heat generation of the catalyst residue in the solid matter, which may be caused by opening the reactor, can be suppressed.

As a temperature of the solvent to be used in the cleaning, it is possible to appropriately set a suitable temperature depending on the partial pressure of the raw material α-olefin at the time of cleaning but the temperature is preferably from 100° C. to 250° C., further preferably from 110° C. to 200° C., and particularly preferably from 130° C. to 190° C.

The concentration of the raw material α-olefin in the solvent to be use at the time of cleaning means one obtained by dividing the weight (kg/Hr) of the α-olefin dissolved in the solvent by the solvent amount (kg/Hr) and representing the product as percentage. The concentration is preferably from 0 to 16 wt % and further preferably from 1 to 8 wt %.

EXAMPLES

The present invention is described further specifically based on Examples. However, the present invention is not limited to the following Examples so long as it does not depart from the gist thereof.

Example 1

<Constitution of Production Steps>

FIG. 1 shows a production flow. There are a completely mixing and stirring type reactor 10 in which ethylene is subjected to low polymerization in the presence of a catalyst, a degassing tank 20 that separates an unreacted ethylene gas from a reaction liquid extracted from the reactor 10, an ethylene separation column 30 that distills ethylene in the reaction liquid extracted from the degassing tank 20, a high boiling matter separation column 40 that separates a high-boiling-point components in the reaction liquid extracted from the ethylene separation column 30, and a 1-hexene separation column 50 that conducts distillation of the reaction liquid extracted from the top of the high boiling matter separation column 40 to distill 1-hexene, and also there are lines 21 (circulation piping) and 12 (first supply piping) that circulates the unreacted ethylene separated in the degassing tank 20 and the condenser 16 to the reactor 10 via a compressor 17. Also, lines 52 (solvent circulation piping) and 13 (second supply piping) that circulate the solvent separated in the 1-hexene separation column 50 to the reactor 10 are provided.

<Conditions at Steady Operation (Production Operation Step)>

From the first supply piping 12, unreacted ethylene separated from the degassing tank 20 and the ethylene separation column 30 is continuously supplied to the reactor 10 via the compressor 17 together with ethylene newly supplied from the ethylene supply piping 12a. Moreover, from the second supply piping 13, the recovered n-heptane solvent separated at the 1-hexene separation column 50 is continuously supplied to the reactor 10 at a flow rate of 25 kg/Hr with by-passing through the solvent drum 60 (0.1 MPaG nitrogen sealing).

Then, from the catalyst supply piping 13a, an n-heptane solution containing chromium(III) 2-ethylhexanoate (a) and 2,5-dimethylpyrrole (b) is supplied in a flow rate of 0.04 L/Hr and is continuously supplied to the reactor 10 via the second supply piping 13. Moreover, an n-heptane solution of triethylaluminum (c) is continuously supplied in a flow rate of 0.04 L/Hr from the third supply piping 14 to the reactor 10. Furthermore, an n-heptane solution of hexachloroethane (d) is continuously supplied in a flow rate of 0.02 L/Hr from the fourth supply piping 15 to the reactor 10.

The solutions of the catalyst components are supplied from tanks (not shown in the FIGURE) sealed with 0.1 MPaG nitrogen.

Incidentally, the catalysts are continuously supplied to the reactor 10 so that the molar ratio of the components in the reactor becomes as follows: (a):(b):(c):(d)=1:25:80:5.

The reaction liquid continuously extracted from the reactor 10 is added with 2-ethylhexanol in a molar ratio of 3.3 relative to triethylaluminum (c) from the deactivator supply piping 11a and thereafter is treated in the 1-hexene separation column 50 via the degassing tank 20, the ethylene separation column 30, the piping 32, and the high boiling matter separation column 40, successively.

The high boiling matter separation column 40 was a normal pressure distillation column in which the concentration part was composed of 2.8 m regular filled materials and the recovery part was composed of sieve trays of four real plates, and was operated under a condition of a reflux ratio of 0.6.

A continuous low polymerization reaction of ethylene was carried out at a reaction temperature of 140° C. under a reaction pressure of 7.0 MPaG for 30 days. Thereafter, a cleaning operation was performed at a liquid temperature of the reactor of 140° C. under a pressure in the reactor of finally 3.0 MPaG.

<Operation Termination Step>

The supply of the catalysts (a), (b), (c), and (d) from the catalyst supply piping 13a, the third supply piping 14, and the fourth supply piping 15 to the reactor was terminated and n-heptane as the solvent was still circulated in the system at 25 Kg/Hr.

In order to prevent temperature drop by the reaction termination, the solvent was heated with the heat exchanger provided on the piping 13 so that the liquid temperature of the reactor became 140° C. At this time, the pressure in the reactor was 7.0 MPaG.

Thereafter, the supply plate to the high boiling matter separation column 40 was switched from the position of the fourth plate counted from the column bottom part (temperature of 101° C.) to the column bottom part (temperature of 157° C.) and the operation was performed under a condition of the reflux ratio of 1.0. The cleaning operation of the reactor was carried out together with each operation of the operation termination step.

With maintaining the temperature of 140° C., the pressure was dropped from 7.0 MPaG to 5.0 MPaG over a period of about 1 hour. After the pressure reached 5.0 MPaG, a liquid sample (1) was collected from the bottom part of the ethylene separation column 30 after the passage of about 10 hours. Thereafter, with still maintaining the temperature of 140° C., the pressure was dropped from 5.0 MPaG to 3.0 MPaG over a period of about 1 hour. After the pressure reached 3.0 MPaG, a liquid sample (2) was collected from the bottom part of the ethylene separation column 30 after the passage of about 10 hours. During this period, no tendency of flooding is observed at the high boiling matter separation column 40 and the operation can be stably performed.

After the sample was subjected to sealed sampling into a metal container, the sample was cooled to room temperature and, after the measurement of weight of the collected liquid, the whole of the polymers in the liquid was filtrated. The filtrated polymers were dried at 80° C. under vacuum for 1 hour by means of a reduced pressure drier and, after cooling, the weight was measured. Furthermore, with regard to the molecular weight of the polymers, a molecular weight distribution in terms of polystyrene was measured on a gel permeation chromatograph Waters GPCV 2000 and an amount of polymers having a molecular weight of 100,000 or more was determined by multiplying the weight of the filtrated polymers by the ratio of the polymers having a molecular weight of 100,000 or more. The polymer concentration in the liquid was calculated by dividing the measured polymer amount (g) by the weight (g) of the liquid.

By the above method, in order to grasp the composition of the supply liquid to the high boiling matter separation column 40, as a result of performing the sampling of the liquid from the column bottom part of the ethylene separation column 30 and measuring the concentration of polymers having a molecular weight of 100,000 or more in n-heptane, the concentration was found to be 610 ppm by weight in the sample (1) and the concentration was found to be 1,110 ppm by weight in the sample (2).

<Termination of Operation of Production Equipments and Open Inspection>

Thereafter, when the circulation in the system was terminated, the equipments are terminated, and the high boiling matter separation column 40 was opened and subjected to internal inspection, no lump-shaped polymers were adhered on the supply plate and the other plates and no fouling was observed. Table-1 shows the results.

Comparative Example 1

The operations were conducted in the same manner as in Example 1 except that no switching of the supply plate in the high boiling matter separation column 40 was performed, the pressure of the reactor at cleaning was maintained at 7.0

MPaG, and, as a liquid sample of the column bottom part of the ethylene separation column 30, a sample (3) after the passage of about 20 hours after the termination of the catalyst supply was only collected. The high boiling matter separation column 40 showed a tendency of flooding and, as a result of open inspection, fouling was observed on the supply plate. Table-1 shows the results. As a result of measuring the concentration of polymers having a molecular weight of 100,000 or more in n-heptane, the concentration was found to be 120 ppm by weight in the sample (3).

Reference Example 1

The continuous low polymerization reaction of ethylene was conducted under the same conditions as in Example 1 for 70 days and a sample (4) was collected by the method described in Example 1 for measuring the polymer concentration of the bottom part of the ethylene separation column 30 at that time. No tendency of flooding was observed in the high boiling matter separation column 40 and, as a result of open inspection, no fouling was also observed on the supply plate. Table-1 shows the results. As a result of measuring the concentration of polymers having a molecular weight of 100,000 or more in n-heptane, the concentration was found to be 50 ppm by weight in the sample (4). Table-1 shows the results

TABLE 1

| | | Example 1 | Comparative Example 1 | Reference Example 1 |
|---|---|---|---|---|
| Polymer concentration* of supply liquid to high boiling matter separation column 40 | ppm by weight | 1110 | 120 | 50 |
| Supply plate of high boiling matter separation column 40 | — | Bottom part | Fourth plate from bottom part | Fourth plate from bottom part |
| Temperature of supply plate of high boiling matter separation column 40 | ° C. | 157 | 101 | 101 |
| Flooding of high boiling matter separation column 40 | — | none | Tendency is observed | none |
| Fouling of supply plate | — | none | observed | none |

*molecular weight of 100,000 or more

In Example 1, since the switching of the supply plate of the high boiling matter separation column 40 was performed in the operation termination step, no flooding occurred in the high boiling matter separation column 40 and precipitation of polymers was not observed on the sieve trays. However, in Comparative Example 1, since the switching of the supply plate of the high boiling matter separation column 40 was not performed although the polymer concentration was 100 ppm by weight or more, the occurrence of a flooding phenomenon was observed and, when the high boiling matter separation column 40 was subjected to open inspection, fouling resulting from the adhesion of lump-shaped polymers was observed on the downcomer part of the supply plate.

In Reference Example 1, since the polymer concentration supplied to the high boiling matter separation column 40 is 100 ppm by weight or less, it is found that flooding does not occur.

Reference Example 2

The production operation step and the operation termination step were carried out under the same conditions as in Example 1. After each of 8 hours, 16 hours, 32 hours, 40 hours, and 56 hours from the time when the liquid temperature of the reactor reached 140° C. and the pressure thereof reached 3.0 MPaG, a liquid was collected as sealed sampling into a metal container from the bottom part of the ethylene separation column 30 and the polymer concentration was measured. On the other hand, sampling into a glass container was performed while a liquid under 0.5 MPaG at the bottom part was flushed into an atmospheric pressure via a valve (i.e., under rapid cooling and stirring conditions), and the shape of the precipitated polymers was observed. Table-2 shows the results.

TABLE 2

| Sample No. | Polymer concentration* [ppm by weight] | Shape of polymers precipitated under flushing conditions |
|---|---|---|
| 1 | 1030 | lump shape and string shape |
| 2 | 370 | lump shape and string shape |
| 3 | 120 | string shape |
| 4 | 90 | granule shape |
| 5 | 20 | granule shape |

*molecular weight of 100,000 or more

In the samples 1 and 2, the precipitation of lump-shaped polymers having a diameter of several centimeters and string-shaped polymers having a length of several centimeters was confirmed. String-shaped polymers having a length of several centimeters were observed in the sample 3 and granule-shaped polymers having a diameter of several millimeters or less were observed in the samples 4 and 5.

Reference Example 3

In the production equipments of an α-olefin oligomer, 0.3 g of the polymers adhered to the inner wall of the reactor were added to a glass-made round-bottom flask containing 150 g of 1-decene and completely dissolved by elevating the temperature to 160° C. Thereafter, upon still standing and cooling at room temperature, granule-shaped polymers having a diameter of several millimeters or less were precipitated in a state dispersed in the solution. Subsequently, when the molecular weight distribution of the polymers was measured in the same manner as in Example 1, the concentration of polymers having a molecular weight of 100,000 or more was found to be 1,590 ppm by weight.

As a result, in the solution where the concentration of polymers having a molecular weight of 100,000 or more is 1,590 ppm by weight or less, it is found that the polymers are precipitated only in the form of a granular shape when the polymers are precipitated in a still standing state.

From the above, it is found that, when the concentration of polymers having a molecular weight of 100,000 or more in the supply liquid exceeds 100 ppm by weight, large-sized polymers are precipitated and adhered at the liquid supply part of the distillation column and cause flooding of the distillation column but the flooding caused by the precipitation of the large-sized polymers can be prevented by changing the position of the supply plate to a position lower than the position at the steady operation (production operation step).

While the invention has been described in detail and with reference to specific embodiments thereof, it will be apparent to one skilled in the art that various changes and modifications can be made therein without departing from the spirit and scope thereof. The present application is based on Japanese Patent Application No. 2015-062877 filed on Mar. 25, 2015, and the contents are incorporated herein by reference.

EXPLANATION OF REFERENCE SIGNS

10 Reactor
10a Stirring machine
11, 22, 32, 33, 41, 42, 51 Piping
11a Deactivator supply piping
12 First supply piping
12a Ethylene supply piping
13 Second supply piping
13a Catalyst supply piping
14 Third supply piping
15 Fourth supply piping
21, 31 Circulation piping
16 Condenser
17 Compressor
20 Degassing tank
30 Ethylene separation column
40 High boiling matter separation column
50 1-Hexene separation column
52 Solvent circulation piping
60 Solvent drum

The invention claimed is:

1. A method for producing an α-olefin oligomer, comprising:
producing the α-olefin oligomer from an α-olefin by a process comprising feeding the α-olefin, a catalyst, and a solvent to a reactor, oligomerizing the α-olefin in the presence of the catalyst and the solvent to produce a reaction product comprising the α-olefin oligomer, and feeding the reaction product to a distillation column to purify the α-olefin oligomer; and
terminating the production of the α-olefin oligomer by a process comprising terminating the feeding of the catalyst to the reactor, and circulating the solvent between the reactor and the distillation column,
wherein the solvent is supplied to the distillation column during the terminating from a feed position lower than a feed position from which the reaction product is supplied to the distillation column during the producing,
the distillation column contains at least one tray or at least one filled material for distillation,
the feed position of the solvent in the terminating is lower than a lowermost tray or a lowermost filled material in the distillation column, and
the solvent circulated between the reactor and the distillation column in the terminating comprises a polymer having a molecular weight of 100,000 or more and produced during the producing.

2. The method according to claim 1, wherein in the terminating, after the feeding of the catalyst to the reactor is terminated, the feed position during the producing is switched to the feed position during the terminating.

3. The method according to claim 2, wherein in the terminating, the solvent circulated between the reactor and the distillation column comprises the polymer in an amount of 100 ppm by weight or more relative to the solvent.

4. The method according to claim 2, wherein in the terminating, temperature inside the distillation column at the feed position is 110° C. or higher.

5. The method according to claim 2, wherein the terminating comprises reducing a partial pressure of the α-olefin at a vapor phase of the reactor in at least two stages.

6. The method according to claim 2, wherein the terminating further comprises cleaning at least one of the reactor and a heat exchanger configured to remove reaction heat.

7. The method according to claim 2, wherein the feed position during the terminating is in a bottom part of the distillation column.

8. The method according to claim 2, wherein the distillation column is a separation column configured to separate a high boiling matter.

9. The method according to claim 8, wherein the distillation column is connected to an α-olefin separation column and a product separation column.

10. The method according to claim 8, wherein the producing further comprises extracting a component having a boiling point higher than a boiling point of the α-olefin oligomer from a bottom part of the distillation column to a tank and storing the component in the tank, and the terminating further comprises circulating the component stored in the tank between the distillation column and the tank.

11. The method according to claim 2, wherein the α-olefin is ethylene and the α-olefin oligomer is an α-olefin having 4 to 10 carbon atoms.

12. The method according to claim 1, wherein in the terminating, the solvent circulated between the reactor and the distillation column comprises the polymer in an amount of 100 ppm by weight or more relative to the solvent.

13. The method according to claim 1, wherein in the terminating, temperature inside the distillation column at the feed position is 110° C. or higher.

14. The method according to claim 1, wherein the terminating comprises reducing a partial pressure of the α-olefin at a vapor phase of the reactor in at least two stages.

15. The method according to claim 1, wherein the terminating further comprises cleaning at least one of the reactor and a heat exchanger configured to remove reaction heat.

16. The method according to claim 1, wherein the feed position during the terminating is in a bottom part of the distillation column.

17. The method according to claim 1, wherein the distillation column is a separation column configured to separate a high boiling matter.

18. The method according to claim 17, wherein the distillation column is connected to an α-olefin separation column and a product separation column.

19. The method according to claim 17, wherein the producing further comprises extracting a component having a boiling point higher than a boiling point of the α-olefin oligomer from a bottom part of the distillation column to a tank and storing the component in the tank, and the terminating further comprises circulating the component stored in the tank between the distillation column and the tank.

20. The method according to claim 1, wherein the α-olefin is ethylene and the α-olefin oligomer is an α-olefin having 4 to 10 carbon atoms.

* * * * *